(12) United States Patent
Cabot

(10) Patent No.: US 12,259,342 B2
(45) Date of Patent: Mar. 25, 2025

(54) HANDHELD INSPECTION DEVICE AND METHOD OF INSPECTING AN INFRASTRUCTURE HAVING A STRUCTURE WALL SUPPORTED INTO MATERIAL

(71) Applicant: INVERSA SYSTEMS LTD., Fredericton (CA)

(72) Inventor: Peter Marc Cabot, Fredericton (CA)

(73) Assignee: INVERSA SYSTEMS LTD., Fredericton (CA)

( * ) Notice: Subject to any disclaimer, the term of this patent is extended or adjusted under 35 U.S.C. 154(b) by 78 days.

(21) Appl. No.: 17/921,135

(22) PCT Filed: Mar. 9, 2021

(86) PCT No.: PCT/CA2021/050311
§ 371 (c)(1),
(2) Date: Oct. 25, 2022

(87) PCT Pub. No.: WO2021/243439
PCT Pub. Date: Dec. 9, 2021

(65) Prior Publication Data
US 2023/0184700 A1     Jun. 15, 2023

Related U.S. Application Data

(60) Provisional application No. 63/033,793, filed on Jun. 2, 2020.

(51) Int. Cl.
*G01N 33/38*     (2006.01)
*G01N 23/203*     (2006.01)

(52) U.S. Cl.
CPC ......... *G01N 23/203* (2013.01); *G01N 33/383* (2013.01); *G01N 2223/053* (2013.01);
(Continued)

(58) Field of Classification Search
None
See application file for complete search history.

(56) References Cited

U.S. PATENT DOCUMENTS 4,140,906 A * 2/1979 Morrison ................. G21F 5/02
378/197
5,195,117 A     3/1993 Ong
(Continued)

*Primary Examiner* — Thomas R Artman
(74) *Attorney, Agent, or Firm* — Reno Lessard; Norton Rose Fulbright Canada LLP

(57) ABSTRACT

There is described a handheld inspection device for inspecting an infrastructure having a structure wall at least partially supported into material such as soil. The handheld inspection device generally has a portable frame; a high energy photon source mounted to said portable frame and having a radioactivity level below a threshold radioactivity level; a scattered photon detector mounted to said portable frame and having a field of view diverging towards said target region of said infrastructure and encompassing at least a portion thereof, said scattered photon detector detecting scatter events incoming from said target region during a given period of time, and generating a signal indicative of scatter events detected during said period of time; and a controller receiving said signal generated by said scattered photon detector; and generating an integrity indication associated to said target region of said infrastructure based on said received signal.

16 Claims, 6 Drawing Sheets

(52) U.S. Cl.
CPC .............. *G01N 2223/1003* (2013.01); *G01N 2223/1013* (2013.01); *G01N 2223/205* (2013.01); *G01N 2223/301* (2013.01); *G01N 2223/631* (2013.01); *G01N 2223/646* (2013.01); *G01N 2223/648* (2013.01)

(56) References Cited

U.S. PATENT DOCUMENTS

| | | | | |
|---|---|---|---|---|
| 6,050,725 | A * | 4/2000 | Regimand | G01N 23/06 250/252.1 |
| 6,735,279 | B1 * | 5/2004 | Jacobs | G01N 23/201 378/86 |
| 7,130,374 | B1 * | 10/2006 | Jacobs | G01N 23/203 378/87 |
| 8,705,694 | B2 * | 4/2014 | Grubsky | G21K 1/025 378/62 |
| 9,091,627 | B2 * | 7/2015 | Troxler | G01N 19/10 |
| 9,599,579 | B2 * | 3/2017 | Durette | G01N 23/046 |
| 10,024,808 | B2 * | 7/2018 | Arsenault | G01N 23/20066 |
| 10,690,578 | B2 * | 6/2020 | Troxler | G01N 9/24 |
| 10,983,074 | B2 * | 4/2021 | Safai | G01N 23/203 |
| 2004/0218714 | A1 * | 11/2004 | Faust | G01T 1/295 378/53 |
| 2006/0256917 | A1 * | 11/2006 | Jacobs | G01N 23/203 378/87 |
| 2011/0122994 | A1 | 5/2011 | Grubsky et al. | |
| 2014/0158897 | A1 * | 6/2014 | Troxler | G01N 23/005 250/390.06 |
| 2015/0377804 | A1 | 12/2015 | Arsenault et al. | |
| 2017/0052126 | A1 * | 2/2017 | Durette | G01N 23/046 |
| 2017/0356832 | A1 * | 12/2017 | St-Onge | E21B 7/00 |
| 2018/0328869 | A1 * | 11/2018 | Safai | G01N 23/203 |
| 2019/0078989 | A1 * | 3/2019 | Troxler | G01N 19/10 |
| 2023/0184700 | A1 * | 6/2023 | Cabot | G01N 23/20 378/57 |
| 2023/0184701 | A1 * | 6/2023 | Cabot | G01N 17/006 378/86 |

* cited by examiner

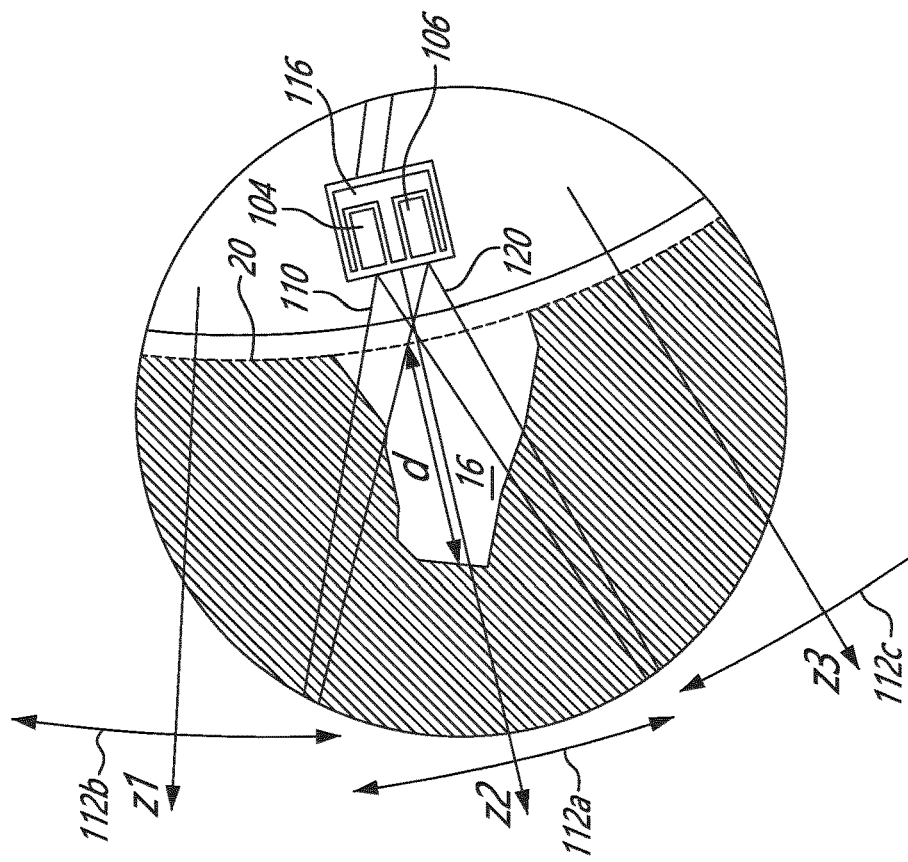
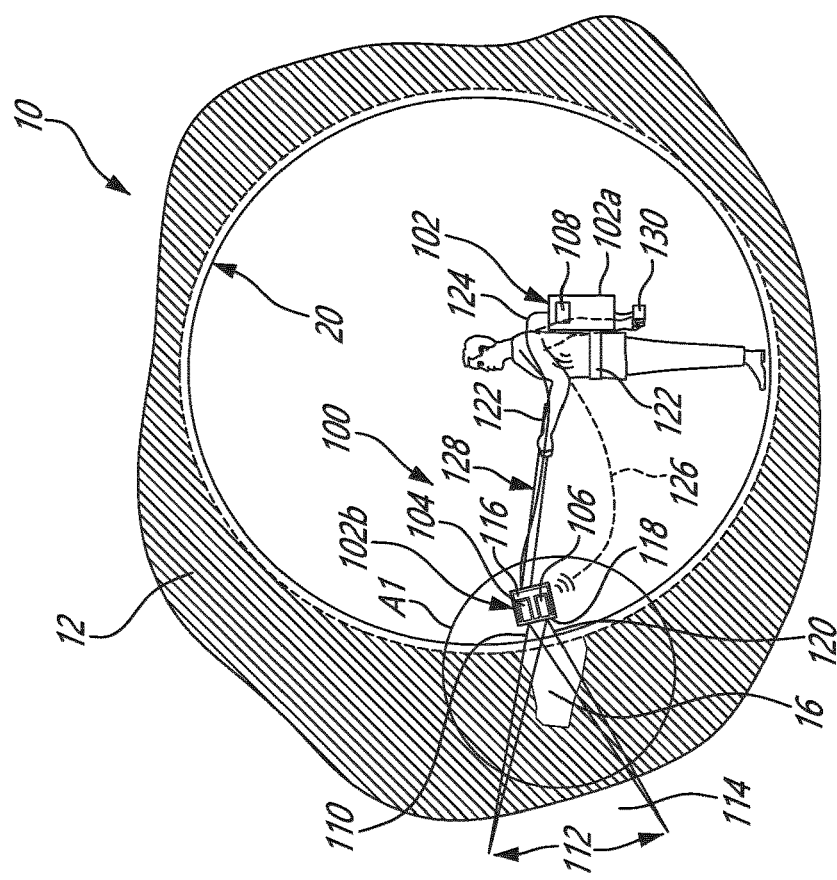
Fig. 1A
Fig. 1

HANDHELD INSPECTION DEVICE AND METHOD OF INSPECTING AN INFRASTRUCTURE HAVING A STRUCTURE WALL SUPPORTED INTO MATERIAL

FIELD

The improvements generally relate to infrastructure inspection and more specifically relate to infrastructure inspection using non-destructive inspection (NDI) and/or non-destructive testing (NDT).

BACKGROUND

Inspecting infrastructure such as culverts, levees, and storm sewers is of relevance in order to address public safety. For instance, such infrastructures can be provided in the form of underground channels allowing passage of water under roadways and are generally obtained by burying a large diameter pipe under soil.

Culverts, levees, and/or storm sewers can deteriorate over time due to, for instance, erosion of the soil surrounding the pipes. As the soil surrounding a pipe gradually erodes, voids can be created between the surrounding soil and the pipe, thus increasing risks of failure (e.g., washout due to flooding). As deterioration of such infrastructure depends on external physical factors, inspecting each infrastructure is key in providing a satisfactory maintenance plan. Preliminary inspection of such infrastructures is typically provided in the form of visual inspection and/or acoustic inspection. When necessary, it is generally known to inspect these infrastructures using sophisticated inspection apparatuses such as the backscatter computed tomography (BCT) device described in U.S. Pat. No. 9,599,579 B2. As such apparatuses can provide a detailed map showing the integrity of the soil behind the structure wall on a point by point basis; they also require a highly radioactive radiation source to generate, in an efficient manner, a sufficient amount of backscatter from each inspected point.

Although existing visual inspection, acoustic inspection and more sophisticated inspection apparatuses are satisfactory to a certain degree, there remains room for improvement.

SUMMARY

In an aspect of the present disclosure, there is described a handheld inspection device for inspecting an infrastructure with a structure wall received into soil. The handheld inspection device generally has a portable frame to which are mounted a high energy photon source and a scattered photon detector. The high energy photon source has a field of radiation which diverges towards a target region of the infrastructure. More specifically, the high energy photon source radiates a photon beam along the field of radiation and penetrates across the structure wall and then through the soil behind the structure wall. The high energy photon source is selected such that it has a radioactivity level below a threshold radioactivity level. In this way, the high energy photon source cannot be identified as a highly radioactive photon source which would otherwise require a minimal amount of safety requirements. The handheld inspection device has a scattered photon detector with a field of view diverging towards the target region of the infrastructure and which encompasses at least a portion of it. The scattered photon detector detects scatter events incoming from the radiated target region during a given period of time, and generates a signal indicative of scatter events detected during the period of time. A controller is generally provided to receive the signal generated by the scattered photon detector, and to generate an indication of the integrity of the infrastructure based on the received signal. The indication of the integrity of the infrastructure may be limited in terms of resolution and/or accuracy, especially as the high energy photon source is of low radioactivity, and as that the field of radiation and the field of view are both divergent. As such, the handheld inspection device may be used as a preliminary inspection device usable to quickly and safely identify areas of unsatisfactory integrity, after which more sophisticated inspection apparatuses can be brought in for further mapping.

In accordance with a first aspect of the present disclosure, there is provided a handheld inspection device for inspecting an infrastructure having a structure wall at least partially supported into material, the handheld inspection device comprising: a portable frame; a high energy photon source mounted to said portable frame and having a field of radiation diverging towards a target region of said infrastructure, said high energy photon source radiating a photon beam along said field of radiation and at least partially penetrating across said structure wall and through said supporting material behind said structure wall, said high energy photon source having a radioactivity level below a threshold radioactivity level; a scattered photon detector mounted to said portable frame and having a field of view diverging towards said target region of said infrastructure and encompassing at least a portion thereof, said scattered photon detector detecting scatter events incoming from said target region during a given period of time, and generating a signal indicative of scatter events detected during said period of time; and a controller communicatively coupled to said scattered photon detector, said controller having a processor and a memory having stored thereon instructions that when executed by said processor perform the steps of: receiving said signal generated by said scattered photon detector; and generating an integrity indication associated to said target region of said infrastructure based on said received signal.

Further in accordance with the first aspect of the present disclosure, said generating said integrity indication can for example comprise determining a void dimension indicative of a dimension of a void in said supporting material behind said structure wall, said void dimension extending along an axis of said field of view.

Still further in accordance with the first aspect of the present disclosure, said void dimension can for example be given by a relation equivalent to the following equation:

$$z = \alpha^{-1} \ln \frac{y(z) - A}{C - A},$$

wherein z denotes said void dimension, y(z) denotes the number of scatter events detected by the scattered photon detector during the period of time, $\alpha$ denotes a constant dependent on said supporting material, A denotes a first reference value indicative of a signal generated by said scattered photon detector when said structure wall is surrounded with no supporting material and C denotes a second reference value indicative of a signal generated by said scattered photon detector when said structure wall is fully surrounded with supporting material.

Still further in accordance with the first aspect of the present disclosure, said period of time can for example be below 5 minutes, preferably below 2 minutes and most preferably below 1 minute.

Still further in accordance with the first aspect of the present disclosure, said target region can for example be at least 20 cm², preferably at least 40 cm² and most preferably at least 80 cm².

Still further in accordance with the first aspect of the present disclosure, said high energy photon source can for example comprise Cesium-137 as an unstable isotope generating said photon beam.

Still further in accordance with the first aspect of the present disclosure, said high energy photon source can for example be monoenergetic, each radiated photon can for example have an energy comprised within an energy bandwidth spanning no more than 50 keV, preferably no more than 20 keV and most preferably no more than 10 keV.

Still further in accordance with the first aspect of the present disclosure, said scattered photon detector can for example have a monoenergetic detection bandwidth spanning no more than 20 keV, preferably no more than 10 keV and most preferably no more than 10 keV.

Still further in accordance with the first aspect of the present disclosure, said portable frame can for example have at least a handle.

Still further in accordance with the first aspect of the present disclosure, said handle can for example be a strap wrapable around an operator's body.

Still further in accordance with the first aspect of the present disclosure, said handle can for example be at least one of flexible and rigid.

Still further in accordance with the first aspect of the present disclosure, said frame can for example have an extension pole to which said high energy photon source and said scattered photon detector are mounted.

Still further in accordance with the first aspect of the present disclosure, the handheld inspection device can for example further comprise a trigger simultaneously triggering said high energy photon source and said scattered photon detector.

In accordance with a second aspect of the present disclosure, there is provided a method of inspecting an infrastructure having a structure wall at least partially supported into material, the method comprising: radiating a photon beam within a field of radiation diverging towards a target region of said infrastructure, said photon beam at least partially penetrating across said structure wall and through said supporting material behind said structure wall, said photon beam having a radioactivity level below a threshold radioactivity level; detecting scatter events incoming from said radiated target region during a given period of time; generating a signal indicative of the scatter events detected during said period of time; and using a controller, generating an integrity indication associated to said target region of said infrastructure based on said received signal.

Further in accordance with the second aspect of the present disclosure, said generating the integrity indication can for example comprise determining a void dimension indicative of a dimension of a void in said supporting material behind said structure wall.

Still further in accordance with the second aspect of the present disclosure, said void dimension can for example be given by a relation equivalent to the following equation:

$$Z = \alpha^{-1} \ln \frac{y(z) - A}{C - A},$$

wherein z denotes said void dimension, y(z) denotes the number of scatter events detected by said scattered photon detector during the period of time, ∝ denotes a constant dependent on said supporting material, A denotes a first reference value indicative of a signal generated by said scattered photon detector when said structure wall is surrounded with no supporting material and C denotes a second reference value indicative of a signal generated by said scattered photon detector when said structure wall is fully surrounded with supporting material.

In accordance with a third aspect of the present disclosure, there is provided a handheld inspection device comprising a portable frame; a high energy photon source mounted to said portable frame and having a radioactivity level below a threshold radioactivity level; a scattered photon detector mounted to said portable frame and having a field of view diverging towards said target region of said infrastructure and encompassing at least a portion thereof, said scattered photon detector detecting scatter events incoming from said target region during a given period of time, and generating a signal indicative of scatter events detected during said period of time. In some embodiments, an optional controller is provided for receiving said signal generated by said scattered photon detector, and generating an integrity indication associated to said target region of said infrastructure based on said received signal. In case where no controller is used, a value indicative of the signal generated by the scattered photon detector can be displayed using a display, light indicators and the like.

Many further features and combinations thereof concerning the present improvements will appear to those skilled in the art following a reading of the instant disclosure.

DESCRIPTION OF THE FIGURES

In the figures,

FIG. 1 is a sectional view of an infrastructure having a corrugated pipe surrounded by soil, showing an operator inspecting the infrastructure using of an exemplary handheld inspection device, in accordance with one or more embodiments;

FIG. 1A is an enlarged view of inset A1 of FIG. 1;

DETAILED DESCRIPTION

Figure 2:
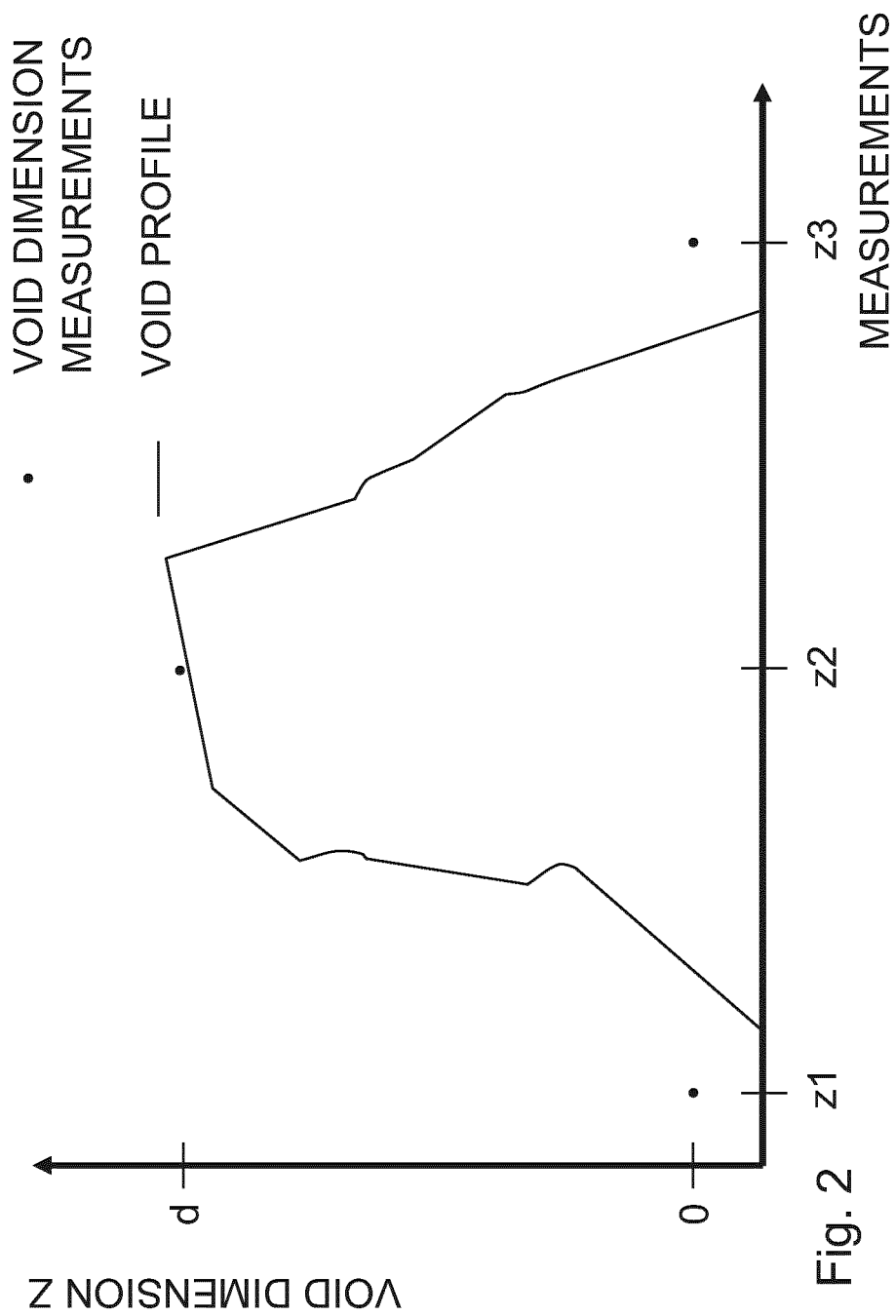
FIG. 2 is a graph showing void dimension for measurements performed using the handheld inspection device of FIG. 1, in accordance with one or more embodiments.

FIG. 1 shows an example of a handheld inspection device 100 for inspecting an infrastructure 10 having a structure wall 20 at least partially supported into material such as soil 12. Other examples of supporting material can include, but not limited to, cement, mortar, grout and any other suitable supporting material.

As depicted, the handheld inspection device 100 has a portable frame 102 to which are mounted a high energy photon source 104 and a scattered photon detector 106. Examples of such a high energy photon source can include, but is not limited to, a gamma ray source comprising an unstable isotope emitting high energy photons from a natural decay process, an x-ray tube, a cyclotron produced radionuclide, a fast neutron source, or any combination thereof. A controller 108 is also communicatively coupled at least to the scattered photon detector 106.

The high energy photon source 104 has a field of radiation 110 which diverges towards a target region 112 of the infrastructure 10. The high energy photon source 104 is used to radiate a photon beam 114 along the field of radiation 110 and at least partially penetrates across the structure wall 20 and through the soil 12 behind said structure wall 20. In some embodiments, the controller 108 may also be communicatively coupled to the high energy photon source 104, to its power supply and/or to a shutter thereof, in order to control the radiation of the photon beam 114.

It is noted that the high energy photon source 104, and/or its photon beam 114, has a radioactivity level below a threshold radioactivity level. For instance, Schedule 1 in Nuclear Substances and Radiation Devices Regulations (SOR/2000-207) under the Nuclear Safety and Control Act (S. C. 1997, c.9) defines the exemption quantities for various isotopes. Cobalt-57 and Cesium-137 have threshold radioactivity levels of $1\times10^6$ and $1\times10^4$ Becquerels (or 100 kBq and 10 kBq), respectively. In some embodiments, the high energy photon source 104 includes two Cesium-137 isotope sources operated at 300 kBq each which may require a license in Canada. In the United States, however, such high energy photon sources do not require a license, as the threshold radioactivity level may be about 370 kBq. The threshold radioactivity level is set so that the high energy photon source 104 cannot be identified as a too radioactive radiation source which would otherwise require a minimal amount of safety requirements. In some embodiments, the threshold radioactivity level may be below 400 kBq, preferably below 375 kBq, and most preferably below 350 kBq. Accordingly, the handheld inspection device 100 can be operated by operators with minimal amount of training and/or minimal backscatter shielding; thereby simplifying the use of the handheld inspection device 100 compared to more sophisticated inspection apparatuses. An example of such a high energy photon source 104 can include, but is not limited to, Cesium-137 as an unstable isotope generating the photon beam 114. However, other high energy photon sources such as Iridium-192, Europium-152 or any suitable unstable isotope may also be used. The high energy photon source 104 can have a shielding member 116 shielding the operator from any of its radiation. The high energy photon source 104 can also have a diverging member 118 ensuring that the field of radiation 110 diverges towards the target region 112. The shielding and diverging members 116 and 118 can be arranged such that the high energy photon source 104 bombards the target region 112 while blocking such radiation from directly reaching the scattered photon detector 106 and/or the operator.

The scattered photon detector 106 has a field of view 120 which diverges towards the target region 112 of the infrastructure 10. As shown, the field of view 120 encompasses at least a portion of the field of radiation 110. In this way, the scattered photon detector 106 detects scatter events incoming from the target region 112 during a given period of time, and generates a signal indicative of the detected scatter events detected during that period of time. Examples of scattered photon detectors can include, but is not limited to, a photomultiplier tube, a scintillator, a solid-state detector, a silicon photo-multiplier, a Geiger-Mueller detector, a liquid scintillation detector and the like. In some preferred embodiment, the scattered photon detector 106 can be provided in the form of a single photon sensitive detector capable of detecting high energy photons in the gamma range of the electromagnetic spectrum. Such scattered photon detectors can be, for example, made up of scintillation crystals coupled with silicon photomultipliers or classical photomultiplier tubes.

Upon receiving the signal generated by the scattered photon detector 106, the controller 108 can generate an integrity indication associated to the target region 112 of the infrastructure 10 based on the received signal. The integrity indication can differ from one embodiment to another. For instance, the integrity indication may be a value representative of the number of scatter event(s) detected during a given period of time. The integrity indication can be indicative of whether the number of scatter events detected during a given period of time exceeds a given number threshold in some embodiments. It is also envisaged that the signal generated by the scattered photon detector 106 be processed using reference data in order to measure a dimension of the void behind the structure wall, if any. The signal generated by the scattered photon detector 106 may be an electrical signal (e.g., analog signal, digital signal) to be processed by a controller for instance. In some embodiments, the signal may also be visual, auditory and/or haptic, as the scattered photon detector 106 may be communicatively coupled to corresponding visual, auditory and/or haptic indicators which render the signal in real time.

In some embodiments, the controller 108 can determine a void dimension indicative of a dimension of a void 16 in the soil 12 behind the structure wall 20, in which the void dimension extends along an axis of the field of view 110 and/or to the field of radiation 120, such as shown in FIG. 1A. As depicted, the handheld inspection device 100 is shown during inspection of a first target region 112a of the infrastructure 10. As shown, the void 16 has a dimension d which can be part of the indication of the integrity of the infrastructure 10 generated by the controller 108. Inspection of second and third target regions 112b and 112c would have otherwise provided an indication that no void is present behind the structure wall 20 or that alternately the void dimension is null, such as shown in the graph of FIG. 2. As depicted in this figure, one can appreciate that the determined void dimensions have a limited resolution as the field of radiation of the high energy photon source and the field of view of the scatted detector are divergent. In any case, the determined void dimensions can nonetheless be used as an indication that there is some kind of void or absence of supporting material behind the structure wall 20 at the first target region 112a which can therefore be tagged or labeled as such for further inspection using more sophisticated devices. For instance, in some embodiments, the inspected target region is at least 20 cm², preferably at least 40 cm² and most preferably at least 80 cm², as measured at 10 cm from the handheld inspection device 100, preferably 50 cm meter from the handheld inspection device 100, and most preferably one meter or more from the handheld inspection device 100.

In some embodiments, the void dimension is given by a relation equivalent to the following equation:

$$Z = \alpha^{-1} \ln \frac{y(z) - A}{C - A}, \quad (1)$$

where z is the void dimension, y(z) is the number of scattered photons detected by the scattered photon detector 106 during the period of time, ∝ denotes a constant dependent on the soil, A denotes a first reference value indicative of a signal generated by a scattered photon detector when a structure wall or similar construction is surrounded with no soil and C denotes a second reference value indicative of a signal generated by a scattered photon detector when a structure wall of similar construction is fully surrounded with soil.

Referring back to FIG. 1, the portable frame 102 shown in this embodiment has one or more handles 122 to be grabbed by one or two hands of the operator. The handle 122 can be provided in the form of one or more straps which can be wrapped around the body or limb(s) of the operator. The handle 122 can be made flexible or rigid depending on the embodiment.

In the illustrated embodiment, the frame 102 has a base portion 102a and a head portion 102b. The head portion 102b comprises both the high energy photon source 104 and the scattered photon detector 106 whereas the base portion 102a comprises the controller 108, in this example. The base portion 102a and the head portion 102b can be communicatively coupled to one another using a wired connection 124, a wireless connection 126 or a combination of both.

As shown, the base portion 102a and the head portion 102b are mechanically coupled to one another using an extension pole 128 which can be made rigid or flexible. The extension pole 128 can be straight or curvilinear. In some embodiments, the extension pole 128 can be an articulated arm having one or more articulations along its length. Additionally or alternatively, the handheld inspection device 100 can have a trigger 130 which can simultaneously trigger the high energy photon source 104 and the scattered photon detector 106. The trigger 130 can be provided for ease of use and can allow the operator to quickly notify the handheld inspection device 100 when it is in position and ready for a measurement to be performed. It is intended that in embodiments where the high energy photon source 104 is a gamma source, it cannot be triggered per se as such sources are based on a radionuclide. However, the trigger 130 may block the photon path or expose it depending on the activation or de-activation of the trigger 130, using a shutter for instance. In embodiments where the high energy photon source 104 is a x-ray source, the trigger 130 may activate or de-activate the power supplied to the source 104.

Multiple styles of head portion can be used to achieve different radiation exposure profiles, thus allowing for multiple application specific head portion designs. Optionally, the head portion 102b may also contain additional device(s). The head portion 102b can be removably attached to the rest of the handheld inspection device 100. For instance, the head portion 102b can be placed with one operator's hand while the rest of the handheld inspection device 100 is held with other operator's hand. Such a configuration may occur when inspecting small diameter pipes where it is not convenient to have a pole mounted device. Accordingly, the extension pole 128 is only optional.

In some embodiments, the base portion 102a encloses power cell(s), charging mechanism(s), voltage regulator(s), signal receiver(s), computational platform(s), data storage system(s), communication driver(s), and/or human interface component(s).

The power cell(s) can comprise on or more lithium polymer cells in series and/or parallel configuration; however, it may also consist of other primary or secondary type power cells. Additional protection such as current flow diodes, fuses, positive temperature coefficient devices, or circuit breakers may also be used in series with the battery cells. In some cases, power can be acquired via the charging connector or by means of some other off board connection.

The charging input can comprise a standard USB port, which can double as a data communication channel if required, and appropriate charging electronics. The charging electronics may interface with the computational platform to provide charge level information. Advanced models may include a wireless charging system.

The voltage regulators provide the required voltage to the CPU, human interface devices, head unit, and any other peripherals requiring power. In the case of the photomultiplier tube, a voltage regulator capable of producing up 1,000 volts may be required. When such a high voltage rail is required, additional voltage calibration and circuit isolation may also be provided through mechanical interfaces or through a digital interface to the computational platform. The signal receivers can consist of any number of amplifiers, isolations devices, rectifiers, shapers, or other analog manipulation components. In some embodiments, the end product of the signal receivers is to provide a signal pattern or simple data bank which can be read by or that will trigger events within the computational platform. The information provided by the data channel(s) must convey some degree of chronological and energy information for each individual photon or a strike count for photons of a predefined energy range within a predefined time period.

The controller 108 can be provided as a combination of hardware and software components. The hardware components can be implemented in the form of a computing device 300, an example of which is described with reference to FIG. 3. Moreover, the software components of the controller can be implemented in the form of a software application.

Figure 3:
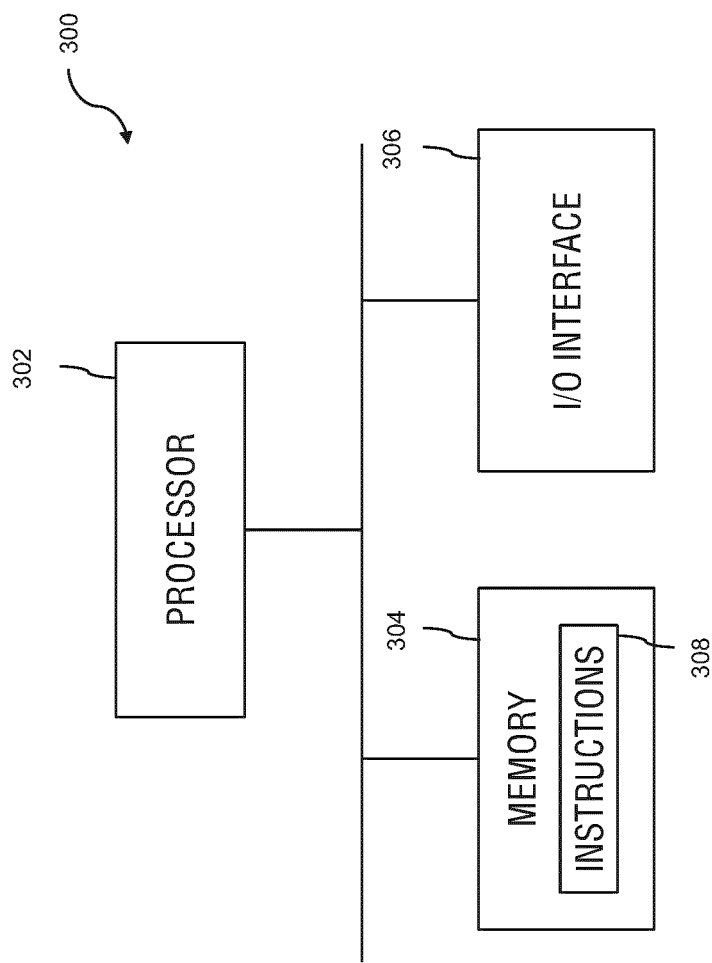
FIG. 3 is a schematic view of an example of a computing device of the handheld inspection device of FIG. 1, in accordance with one or more embodiments.

Referring to FIG. 3, the computing device 300 can have a processor 302, a memory 304, and I/O interface 306. Instructions 308 for performing a method of inspecting an infrastructure using the handheld inspection device 100 of FIG. 1, including instructions for processing the signal received from the scattered photon detector 106 for the purpose of determining a void dimension, can be stored on the memory 304 and accessible by the processor 302.

The processor 302 can be, for example, a general-purpose microprocessor or microcontroller, a digital signal processing (DSP) processor, an integrated circuit, a field programmable gate array (FPGA), a reconfigurable processor, a programmable read-only memory (PROM), or any combination thereof.

The memory 304 can include a suitable combination of any type of non-transitory, computer-readable memory that is located either internally or externally such as, for example, random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), Ferroelectric RAM (FRAM) or the like.

In some embodiments, there can be two basic options for data logging: internal and external. Internal data logging requires some form of non-volatile memory such as an SD Card. External logging requires the presence of some device attached via one of the external digital communication channels. Each embodiment has its own advantage and disadvantage. Internal data logging has the advantage of being more streamlined and reliable since there may not be any required data communication channels which can be interrupted. External data logging requires the user to have additional hardware (such as an android powered tablet) to perform the data logging for them. It does, however, have the advantage of performing computational operations on the data as it is acquired which the base unit itself is not capable of. For example, an android device can present the user with an up to date view of the pipe measurement grid so that inspection decisions can be made on the spot rather than waiting for the data to be uploaded and analyzed later on. Additionally, the cellular connectivity of the mobile platform can be leveraged to update the project data quickly allowing for decisions and directives to be made by the project manager remotely before the field crew leaves the site.

Each I/O interface 306 enables the computing device 300 to interconnect with one or more input devices, such as computer mouse(s), keyboard(s), trigger(s), scattered photon detector(s), or with one or more output devices such as a display, a memory system for storing the generated data, a communication unit for communicating the generated data to an external network.

Each I/O interface 306 enables the controller to communicate with other components, to exchange data with other components, to access and connect to network resources, to server applications, and perform other computing applications by connecting to a network (or multiple networks) capable of carrying data including the Internet, Ethernet, plain old telephone service (POTS) line, public switch telephone network (PSTN), integrated services digital network (ISDN), digital subscriber line (DSL), coaxial cable, fiber optics, satellite, mobile, wireless (e.g. Wi-Fi, WiMAX), SS7 signaling network, fixed line, local area network, wide area network, and others, including any combination of these.

In some embodiments, the I/O interface 306 can comprise external digital communication channels with a wired or wireless digital communication driver along with any necessary hardware (such as antennae or physical connection ports). Some examples of which are Bluetooth, WiFi, RS-232 Serial, USB, and NFC (Near-Field Communication). Additionally, a wired communication channel can be employed through an added connection port or through the same USB port used by the charging mechanism.

The I/O interface 306 can have many different types of components. Typically, a small screen and keypad will suffice. However, additional items such as an external trigger or an LED bank can also be added. Interface to the CPU can be made via GPIO (General Purpose Input/Output) lines, a centralized system bus (such as 12C or some other serialized peripheral bus). It is also possible to build in a mobile platform to provide such an interface (such as an Android powered platform). In the case of remote operation, such interfaces can be omitted in favor of a remote-control system via one or more of the digital communication channels.

The computing device 300 described above is meant to be an example only. Other suitable embodiments of the controller can also be provided, as it will be apparent to the skilled reader.

Figure 4:
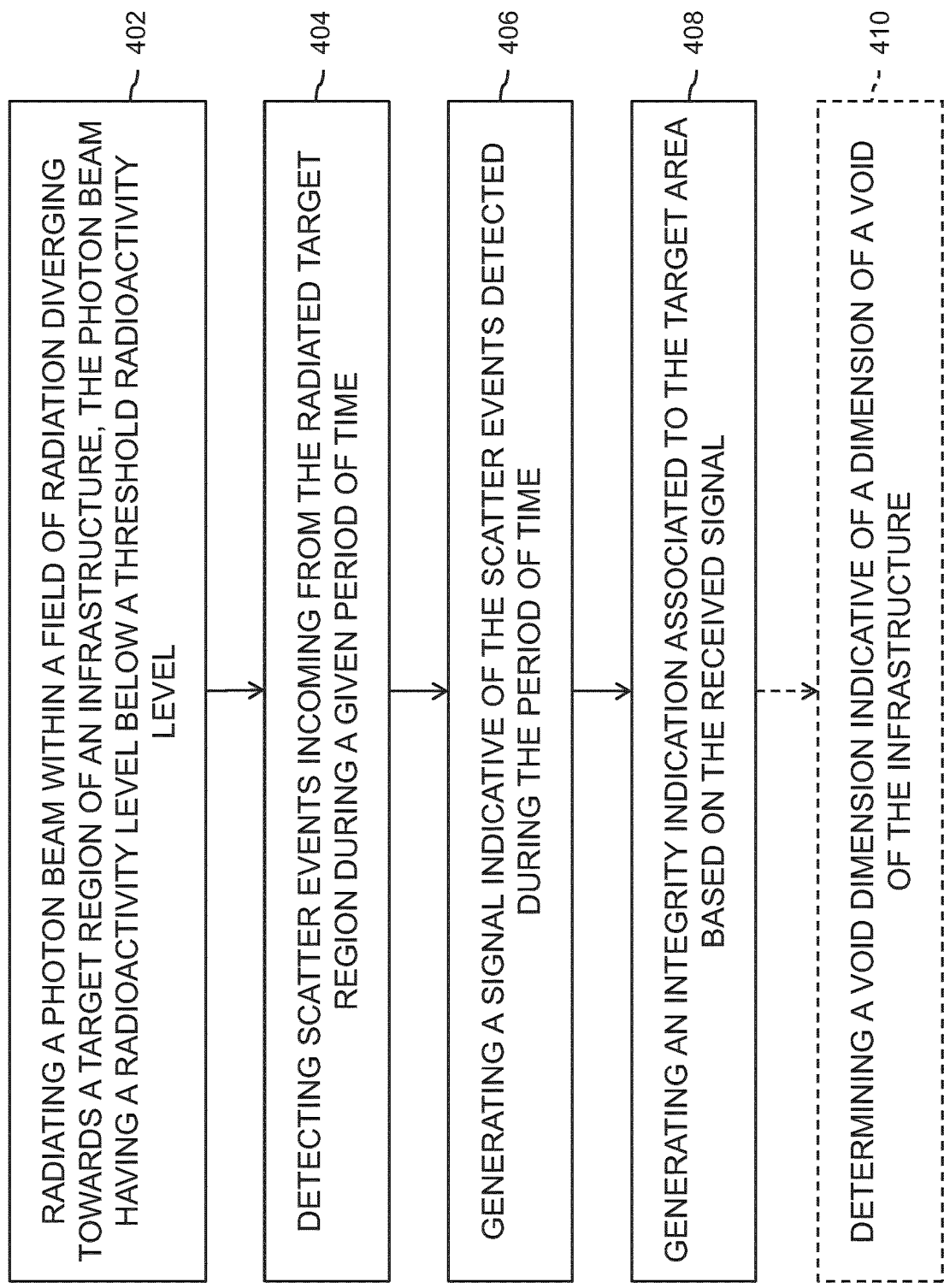
FIG. 4 is a flow chart of an example of a method for inspecting an infrastructure having a structure wall at least partially received into soil, in accordance with one or more embodiments.

Reference is now made to FIG. 4 which illustrates a flow chart of a method 400 of inspecting an infrastructure having a structure wall at least partially received into soil.

At step 402, the high energy photon source radiates a photon beam within a field of radiation diverging towards a target region of the infrastructure. By doing so, the photon beam at least partially penetrates across the structure wall and through the soil behind the structure wall. As mentioned above, it is noted that the photon beam has a radioactivity level below a threshold radioactivity level. In some embodiments, the high energy photon source is monoenergetic in which case each radiated photon has an energy comprised within an energy bandwidth spanning no more than 50 keV, preferably no more than 20 keV and most preferably no more than 10 keV.

At step 404, the scattered photon detector detects scatter events incoming from the radiated target region during a given period of time. In some embodiments, that period of time can be below 1 minute, preferably below 30 seconds and most preferably below 10 seconds, which may allow swift inspections to be performed. When the high energy photon source is monoenergetic, the scattered photon detector can have a monoenergetic detection bandwidth matched to the energy bandwidth of the high energy photon source. For instance, the monoenergetic detection bandwidth may span no more than 20 keV, preferably no more than 10 keV and most preferably no more than 10 keV, depending on the embodiment. In some embodiments, it may preferable for backscattered photons to be in the range of 100 to 200 keV however it is not necessary in some embodiments.

In some embodiments, the handheld inspection device can record the entire spectrum (e.g., from 0 to 255 keV) and log it for later consultation and/or processing. Energy filtering can thus be made later in a post-processing manner. Such post-processing can allow to change the desired energy window after the acquisition, if desired. However, recording the entire spectrum may not be necessary. If cost savings are sought, the windowing can be applied in real time by the controller and thereby only record the final count.

At step 406, the scattered photon detector generates a signal indicative of the scatter events detected during the period of time.

At step 408, the controller generates an integrity indication associated to the target region of the infrastructure based on the received signal. As discussed above, the steps 406 and 408 can be performed sequentially to one another during a live inspection in some embodiments. In such embodiments, an auditory, visual and/or haptic indication may be rendered in real time or quasi real time using corresponding indicators communicatively coupled to the scattered photon detector and/or to the controller. However, in some other embodiments, the step 406 may be performed on-site whereas the step 408, and other post-processing steps, can be performed later. As such, the generated signals are stored on a memory system which is accessible by a processor for later post-processing.

At step 410, the controller can determine a void dimension indicative of a dimension of a void behind the structure wall. It is envisaged that the step 410 is only optional and can therefore be omitted in some embodiments.

Equation (1) described above can be obtained following the reasoning described in the following paragraphs. All measurements can be made by classifying individual photons into approximate energy bins within an energy spectrum. Each measurement can result in a histogram of signal strength for each energy bin within a specific range. The range may be defined by such factors as application and isotope. For example, a Cesium 132 isotope has a strong 622 kEv photon emission. In order to isolate signals from signal scatter events located X cm from the detector face with the source—detector distance also at X cm, the Compton energy shift formula can be used to calculate the energy range that needs to be examined given the initial energy source (e.g., 622 kEv) and/or the scatter angle. In some embodiments, the scatter angle may be 135 degrees. However, it is intended that the actual scatter angle can vary depending on the design of the head portion and on the location of the supporting material (e.g., soil) and/or of the wall structure. Note that the energy distribution may be used to calculate the most likely scatter angle and, therefore, help find the structure wall for inspection purposes.

The first stage of data processing can be to select an energy range of interest and compute the total number of counts within that range. This can be done by integrating the histogram data set for each measurement from the lower energy bounds to the upper energy bounds.

$$\sum_{i=Lower\ Energy\ Bound}^{Upper\ Energy\ Bound} Sig(i), \quad (2)$$

where Sig (i) is the signal at energy i.

The count value can be used to determine the certainty by using a Poisson distribution or, if the count is high enough, a normal approximation. The primary unit to analyze is the normalized CPS (Counts per Second) value.

$$\sum_{i=Lower\ Energy\ Bound}^{Upper\ Energy\ Bound} Sig(i)/Time(i); \quad (3)$$

where Sig(i) is the signal at energy i and Time(i) is the amount of time spent measuring Sig(i).

The above sums can be performed for each measurement resulting in a CPS and count value for each measurement taken. These values will be referred to as $CPS_i$ and $Count_i$ where i is the measurement enumeration ranging from 0 to n−1 where n is the total number of measurements that are performed by the handheld inspection device.

In the Insight Lite application, one can sought to determine which location in the pipe (as represented by a single measurement) should be prioritized for follow up using additional inspection methods such as BCT. Such areas can be identified by the lack of material behind the culvert wall. This lack of material, or "voiding", can present the incoming photons with less material for Compton scattering within the required depth given by the energy range chosen in the first stage of processing. The lowered probability of Compton scatter results in a lower probability of photons being directed back to the detection volume and a lower CPS value.

The exact CPS threshold to determine voided area can depend on many factors such as source strength, detector efficiency, measurement integrity, culvert wall thickness, and/or backfill type. Furthermore, one must determine how much void is an issue for the asset under inspection. For instance, a threshold may have to be determined depending on the type of supporting material behind the structure wall, and/or the type of structure wall that is to be inspected. A simple comparison of measurements within a full data set (e.g., a collection of measurements along an entire asset) can be used by taking the all measurements lower than the mean value to prioritize inspection points, however this assumes that there exists flaws within the asset significant enough to create a range that extends from "unhealthy" to "healthy." This may not always be the case. If a pipe were to be in excellent conditions, this method will yield a set of inspection points at roughly half of the total number of inspection points, distributed randomly along the pipe due to the variability and noise present within each measurement placing them evenly above and below the mean.

A second method can include the measurement of a known good point and a known bad point. Each measurement can be classified relative to their proximity to the known good and known bad points. A challenge with this method is that the size of the void may not scale linearly with CPS value. For example, a 2 mm void may present a significantly smaller CPS value than a 1 mm void, however a 6 mm void may be indistinguishable from a 10 mm void.

It is ultimately desirable for each measurement to be translated to a void size. This cannot be directly calculated using the measured values since each incremental unit of void effects the CPS value nonlinearly along the depth axis of the measurement. However, since the incremental increases in voids beyond a certain point becomes trivial, one can create a fair trade off by calculating an "Equivalent Soil Loss" or ESL. The ESL value can represent the size of the void along the depth axis assuming it is present immediately behind the culvert wall, for instance in a the worst-case scenario. The ESL conversion represents the second processing stage.

Through simple physical modeling, the backscatter computations for a void which increases behind a metal wall (of fixed gauge) can be generalized as follows:

$$y(z)=A+(C-A)e^{\alpha z} \quad (4)$$

y(z) represents the CPS value expected given a void measurement (z) made on the depth axis starting immediately behind the metal wall. A represents the expected CPS value with no fill present. This can be found experimentally by performing a single measurement with only a representative metal plate against the detection surface. The measured value represents a baseline that accounts for such values as noise, leakage, multiple scattering through the plate, and the scatter through open air. C represents a value indicative of the signal with optimal fill (no voids). Both A and C can be measured directly from prebuilt calibration blocks at the beginning of each scan. In some embodiments, A and C can be measured on site by inspecting reference structure wall portions that are either known to have void therebehind or known be satisfactorily buried into soil. In some embodiments A and C can be fetched from a memory system accessible by the controller. α represents a system constant dependent on the supporting material. In our case the supporting material varies little from site to site and can be found experimentally using the following equation:

$$\alpha = Z^{-1}\ln\frac{y(z)-A}{C-A} \quad (5)$$

Lab experiments using multiple void sizes and metal plate thicknesses have shown this constant in the vicinity of:

$$\alpha=-0.23\ cm^{-1} \quad (6)$$

A slight variation of the above equation can be used to calculate Equivalent Soil Loss given a measurement value as follows:

$$Z = -0.23 \text{ cm}^{-1} \ln \frac{y(z) - A}{C - A} \quad (7)$$

Assuming that α is calculated to sufficient accuracy, it can be omitted from any error calculations. Error calculations can be drawn from the two values calculated in the first phase of the data processing; counts and time. The counts for a backscatter system following a Poisson statistical distribution. The measurement device can be programmed such that each measurement requires a minimum number of counts before completing. This number should be of sufficient quantity to allow for a Gaussian approximation to the Poisson distribution. As a result of the normal distribution, one can utilize something called 'confidence intervals' to calculate the error.

A third method can be to calculate the number of standard deviations that each measurement falls from a standard measurement indicative of a healthy measurement. The baseline measurement would still need to be computed for each pipe in order to consider all variations present from site to site in these embodiments.

Figure 5:
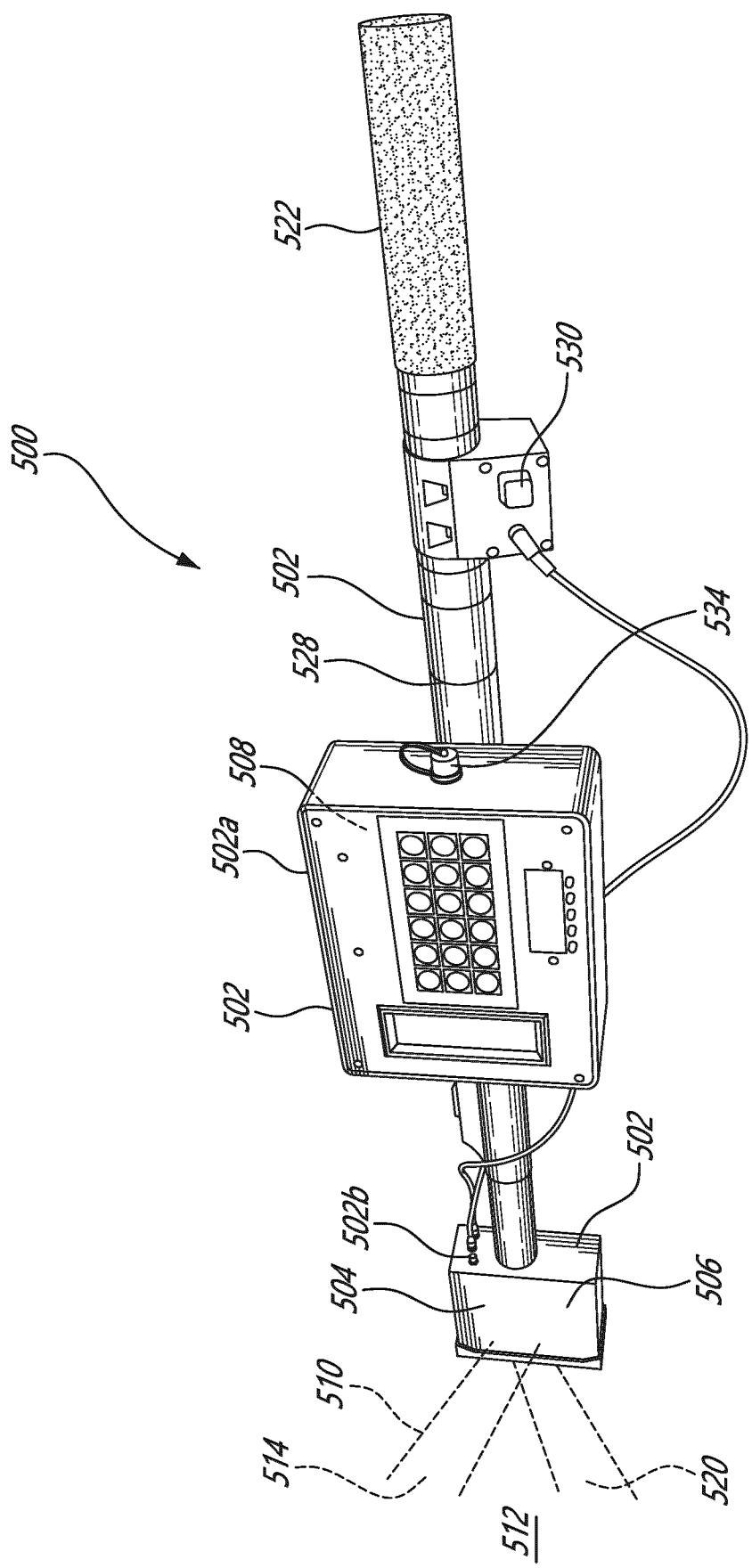
FIG. 5 is a schematic view of an example of a handheld inspection device, in accordance with one or more embodiments.

FIG. 5 shows an example of a handheld inspection device 500. As depicted, the handheld inspection device 500 has a portable frame 502 to which are mounted a high energy photon source 504 and a scattered photon detector 506. As discussed above, the high energy photon source 504 has a divergent field of radiation 510 along which is radiated a photon beam 514 with a radioactivity level below a threshold radioactivity level. The threshold radioactivity level can differ from one embodiment to another. The scattered photon detector 506 has a divergent field of view 520 encompassing at least a portion of the divergent field of radiation 510 of the high energy photon source 504. As shown, the scattered photon detector 506 detects scatter events incoming from a target region 512 during a given period of time, and generates a signal indicative of scatter events detected during that period of time.

In this example, the frame 502 has a head portion 102b enclosing the high energy photon source 504 and the scattered photon detector 506, and a base portion 102a enclosing a controller 508. In this example, the controller 508 has a user interface comprising a keyboard, a first type of visual indicator along with a second type of visual indicator. A communication and/or power supply port 534 is also provided.

In some embodiments, the frame 502 has an extension pole 528 to which the head portion 102b, i.e., the high energy photon source 504 and the scattered photon detector 506, is mounted. The frame has a handle 522 which is in this case provided as an end of the extension pole 528. Gripping material may cover that end for enhancing the grip of an operator's hand. As depicted, a trigger 530 is provided proximate to the handle 522. In this way, the operator can conveniently trigger on or off the measurements by toggling the trigger 530.

Figure 6:
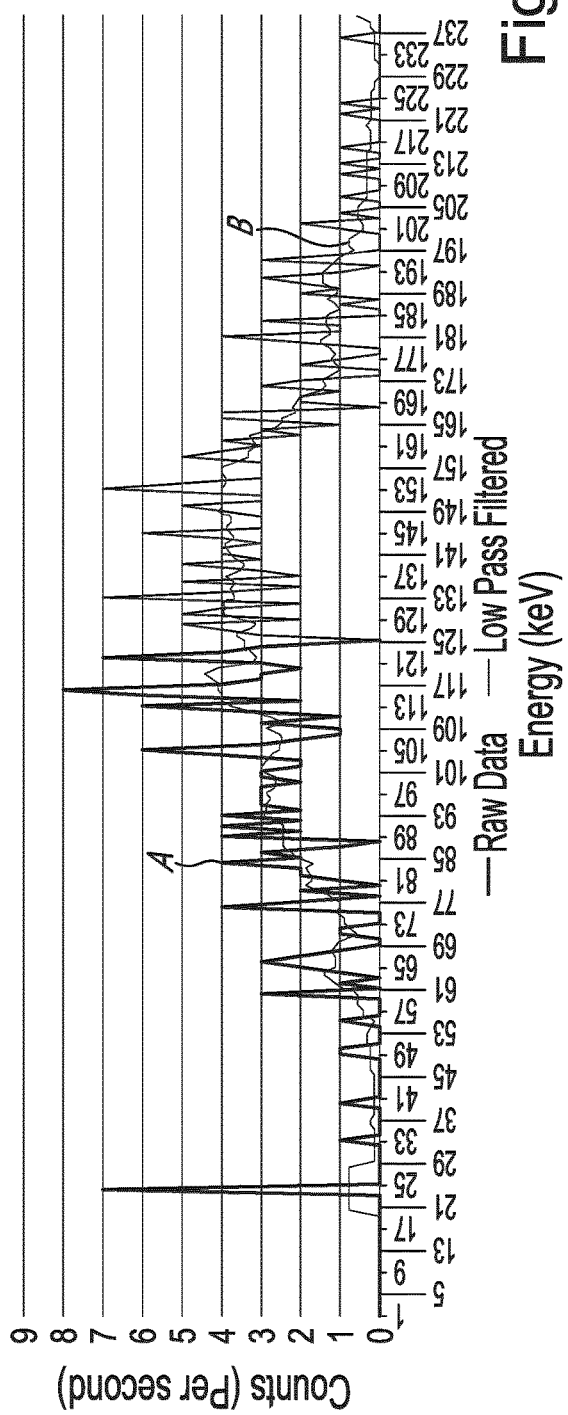
FIG. 6 is a graph showing a count of scatter events as a function of an energy of the detected scatter events, resulting from the inspection of a pipe using the handheld inspection device of FIG. 5, in accordance with one or more embodiments.

FIG. 6 shows an example of scatter events detected by the scattered photon detector 506 following radiation of the photon beam 514 across the target region 512. In this example, the scattered photon detector 506 is polyenergetic as it detects, records and logs scattered photons distributed across a range of energy levels. In this specific example, the controller 508 may receive signal(s) from the scattered photon detector 506 and generate an integrity indication associated to the target region 512 based on the received signal. In some embodiments, it may be preferable to record and log the scattered photons of all energy level, as shown per the raw data curve A. The controller 508 may post-process the raw data by filtering the raw data, e.g., by passing it through a low pass filter such as shown by low pass filtered curve B. The controller 508 may then count the strikes in one or more energy band(s) of interest, e.g., usually from 100 to around 180 keV, depending on the application. Afterwards, the integrity indication can be provided in the form of an integrity map using the raw and/or filtered data.

Figure 7:
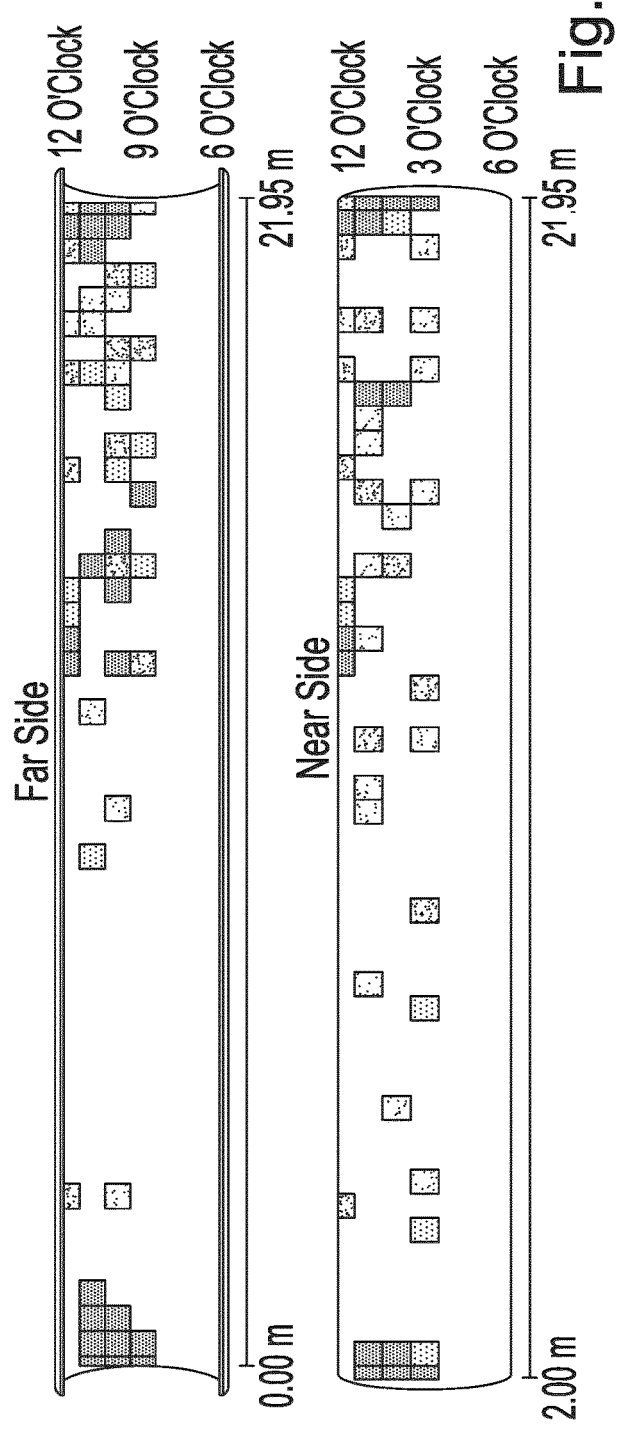
FIG. 7 is a map comprising integrity indicators as a function of spatial coordinates resulting from the inspection of a pipe using the handheld inspection device of FIG. 5, in accordance with one or more embodiments.

FIG. 7 shows an example of an integrity map comprising integrity indicators as a function of spatial coordinates matched to spatial coordinates of the pipe that was inspected using the handheld inspection device 500. The determined integrity indicator can be compared to a corresponding threshold for mapping purposes. As shown, colored areas show target regions of unsatisfactory integrity whereas white or paler areas show target regions having a satisfactory integrity. As can be understood, the raw data may be stored for a given period of time as other useful ways to process the raw data, and more specifically the spectral distribution of the detected scattered photons may appear. For instance, analyzing not only the absolute count within a certain energy window, but the distribution of the count as well, as it may yield satisfactory integrity indicators.

As can be understood, the examples described above and illustrated are intended to be exemplary only. The scope is indicated by the appended claims.

What is claimed is:

1. A handheld inspection device for inspecting an infrastructure having a structure wall at least partially supported into material, the handheld inspection device comprising:
   a portable frame;
   one or more high energy photon source mounted to said portable frame and having a field of radiation diverging towards a target region of said infrastructure, said high energy photon source radiating a photon beam along said field of radiation and at least partially penetrating across said structure wall and through said supporting material behind said structure wall, said one or more high energy photon source each having a radioactivity level of 400 kBq or below;
   a scattered photon detector mounted to said portable frame and having a field of view diverging towards said target region of said infrastructure and encompassing at least a portion thereof, said scattered photon detector detecting scatter events incoming from said target region during a given period of time, and generating a signal indicative of scatter events detected during said period of time; and
   a controller communicatively coupled to said scattered photon detector, said controller having a processor and a non-transitory memory having stored thereon instructions that when executed by said processor perform the steps of:
      receiving said signal generated by said scattered photon detector; and
      generating an integrity indication associated to said target region of said infrastructure based on said received signal.

2. The handheld inspection device of claim 1 wherein said generating said integrity indication comprises determining a void dimension indicative of a dimension of a void in said supporting material behind said structure wall, said void dimension extending along an axis of said field of view.

3. The handheld inspection device of claim 2 wherein said void dimension is given by a relation equivalent to the following equation:

$$Z = \alpha^{-1} \ln \frac{y(z) - A}{C - A},$$

wherein z denotes said void dimension, y(z) denotes the number of scatter events detected by the scattered photon detector during the period of time, ∝ denotes a constant dependent on said supporting material, A denotes a first reference value indicative of a signal generated by said scattered photon detector when said structure wall is surrounded with no supporting material and C denotes a second reference value indicative of a signal generated by said scattered photon detector when said structure wall is fully surrounded with supporting material.

4. The handheld inspection device of claim 1 wherein said period of time is below 5 minutes.

5. The handheld inspection device of claim 1 wherein said target region is at least 20 cm².

6. The handheld inspection device of claim 1 wherein said high energy photon source comprises Cesium-137 as an unstable isotope generating said photon beam.

7. The handheld inspection device of claim 1 wherein said high energy photon source is monoenergetic, each radiated photon having an energy comprised within an energy bandwidth spanning no more than 50 keV.

8. The handheld inspection device of claim 1 wherein said scattered photon detector has a monoenergetic detection bandwidth spanning no more than 20 keV.

9. The handheld inspection device of claim 1 wherein said portable frame has at least a handle.

10. The handheld inspection device of claim 9 wherein said handle is a strap wrapable around an operator's body.

11. The handheld inspection device of claim 9 wherein said handle is at least one of flexible and rigid.

12. The handheld inspection device of claim 1 wherein said frame has an extension pole to which said high energy photon source and said scattered photon detector are mounted.

13. The handheld inspection device of claim 1 further comprising a trigger simultaneously triggering said high energy photon source and said scattered photon detector.

14. A method of inspecting an infrastructure having a structure wall at least partially supported into material, the method comprising:
- radiating a photon beam within a field of radiation diverging towards a target region of said infrastructure, said photon beam at least partially penetrating across said structure wall and through said supporting material behind said structure wall, said photon beam having a radioactivity level of 400 kBq or below;
- detecting scatter events incoming from said radiated target region during a given period of time;
- generating a signal indicative of the scatter events detected during said period of time; and
- using a controller, generating an integrity indication associated to said target region of said infrastructure based on said received signal.

15. The method of claim 14 wherein said generating the integrity indication comprises determining a void dimension indicative of a dimension of a void in said supporting material behind said structure wall.

16. The method of claim 15 wherein said void dimension is given by a relation equivalent to the following equation:

$$Z = \alpha^{-1} \ln \frac{y(z) - A}{C - A},$$

wherein z denotes said void dimension, y(z) denotes the number of scatter events detected by said scattered photon detector during the period of time, ∝ denotes a constant dependent on said supporting material, A denotes a first reference value indicative of a signal generated by said scattered photon detector when said structure wall is surrounded with no supporting material and C denotes a second reference value indicative of a signal generated by said scattered photon detector when said structure wall is fully surrounded with supporting material.

\* \* \* \* \*